United States Patent [19]

Sui et al.

[11] Patent Number: 6,077,869

[45] Date of Patent: Jun. 20, 2000

[54] ARYL PHENYLHYDRAZIDES AS SELECTIVE COX-2 INHIBITORS FOR TREATMENT OF INFLAMMATION

[75] Inventors: Zhihua Sui, Flemington; Michael Wachter, Bloomsbury, both of N.J.

[73] Assignee: Ortho-McNeil Pharmaceutical, Inc., Raritan, N.J.

[21] Appl. No.: 09/421,566

[22] Filed: Oct. 20, 1999

Related U.S. Application Data

[60] Provisional application No. 60/106,101, Oct. 29, 1998.

[51] Int. Cl.⁷ ................................................... A61K 31/16
[52] U.S. Cl. .............................................................. 514/615
[58] Field of Search ............................................. 514/615

[56] References Cited

FOREIGN PATENT DOCUMENTS

410834 A1  1/1991  European Pat. Off. .

OTHER PUBLICATIONS

Ghiglieri–Bertez et al, European Journal of Medicinal Chemistry, vol. 22, pp. 147–152, 1987.

Primary Examiner—William R. A. Jarvis
Attorney, Agent, or Firm—Kenneth J. Dow

[57] ABSTRACT

This invention relates to the use of compounds of formula I as selective COX-2 inhibitors and antiinflammatory agents:

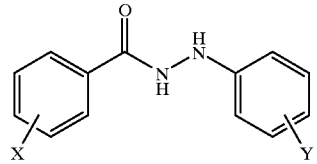

wherein:
X and Y are selected from hydrogen, halogen, alkyl, nitro, amino or other oxygen and sulfur containing functional groups such as hydroxy, methoxy and methylsulfonyl.

1 Claim, No Drawings

ARYL PHENYLHYDRAZIDES AS SELECTIVE COX-2 INHIBITORS FOR TREATMENT OF INFLAMMATION

This application claims the benefit of U.S. Provisional Application Ser. No. 60/106,101 filed Oct. 29, 1998.

FIELD OF THE INVENTION

This invention relates to certain aryl phenylhydrazides for their use as

BACKGROUND OF THE INVENTION

The principal pharmacological effects of nonsteroidal anti-inflammatory drugs (NSAIDs) are due to their ability to inhibit prostaglandin synthesis by blocking the cyclooxygenase activities.[1–6] Prostaglandins are derived from arachidonic acid and the their biosynthesis occurs in three stages: (1) hydrolysis of arachidonate from phospholipid precursors, most likely catalyzed by phospholipase $A_2$; (2) oxygenation of arachidonate to prostaglandin endoperoxide $H_2$ ($PGH_2$), catalyzed by two closely related isozymes, prostaglandin endoperoxide H synthase-1 and -2 (i.e. cyclooxygenase-1 and -2 or COX-1 and COX-2); (3) conversion of $PGH_2$ to a biologically active end-product (e.g. $PGE_2$, $PGF_{2a}$, $PGI_2$), catalyzed by individual enzymes. Compounds which inhibit prostaglandin synthesis are antiinflammatory, anti-pyretic and analgesic. Common side effects of NSAIDs frequently limit their therapeutic use. Typical side effects associated with NSAID therapy are gastrointestinal (GI) and renal. These side effects were believed to be inseparable from the pharmacological effects since prostaglandins have cytoprotective effects in the gastrointestinal tract and also regulate renal blood flow.

The discovery that there are two isozymes, cyclooxygenase-1 (COX-1) and cyclooxygenase-2 (COX-2), that catalyze the second step in prostaglandin synthesis has provided the possibility to separate the 1 pharmacological effects from the side effects of NSAIDs. Research results suggest that the COX-1 and COX-2 belong to separate prostaglandin-forming systems. COX-1 is expressed constitutively in most cells and tissues.[7–9] The COX-1-dependent pathway can respond instantaneously and produces prostaglandins that regulate acute events such as vascular homeostasis. The synthesis of prostagladins by COX-1 also helps maintain normal stomach and renal function. COX-2 is only expressed following mitogenic or inflammatory stimuli. Since it is not expressed in most resting tissues and must be induced, prostaglandins produced by COX-2 are probably involved only secondarily in prolonged physiological reactions. This discovery has now given a reason to believe that the gastrointestinal and renal side effects of the nonsteroidal antiinflammatory drugs can be avoided.

SUMMARY OF THE INVENTION

The invention relates to the use of compounds of formula I as selective COX-2 inhibitors and antiinflammatory agents:

I

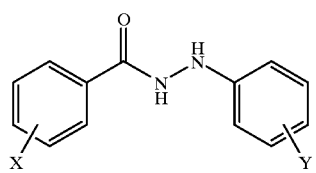

wherein:

X and Y are selected from hydrogen, halogen, alkyl, nitro, amino or other oxygen and sulfur containing functional groups such as hydroxy, methoxy and methylsulfonyl.

Thus, the present invention is a method to alleviate inflammation in a mammal exhibiting an inflammatory condition, the method comprising administering to the mammal an effective amount of a pharmaceutical composition containing a unit dose of the compounds of formula I in association with a pharmaceutically acceptable carrier.

DETAILED DESCRIPTION

The compounds of formula I are synthesized by standard literature procedures as shown in Scheme I.

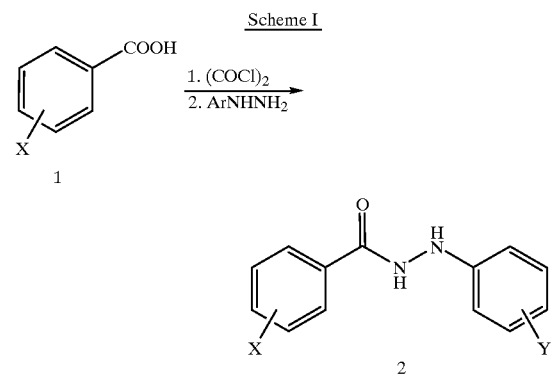

Scheme I

TABLE I

Physical Data of Representative Compounds

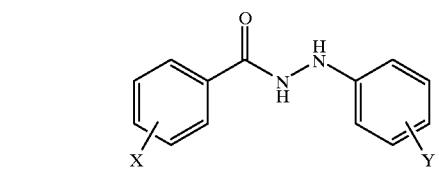

| Example | X | Y | M.P. ° C. | [M + H]$^+$ | Yield % |
|---|---|---|---|---|---|
| 1 | 4-Cl | 4-Cl | 181–182 | 281 | 100 |
| 2 | H | H | 172–173 | 213 | 85 |
| 3 | 4-Cl | H | 174–175 | 247 | 80 |
| 4 | H | 4-CH$_3$ | 80–82 | 227 | 87 |
| 5 | H | 4-Cl | 154–156 | 247 | 72 |
| 6 | H | 4-SO$_2$Me | 209–210 | 291 | 65 |
| 7 | 4-Cl | 4-Me | 216–217 | 261 | 72 |
| 8 | 4-Cl | 4-SO$_2$Me | 209–210 | 325 | 56 |
| 9 | 4-MeO | 4-Cl | 200–201 | 277 | 47 |
| 10 | 4-Cl | 4-Ome | 145–146 | 277 | 78 |
| 11 | 4-OMe | H | 174–175.5 | 243 | 75 |
| 12 | H | 4-Ome | 140–141 | 243 | 99 |

Procedure I was used to determine the ability of the compounds to inhibit cyclooxygenase 2 (6217/6218). Sheep seminal vesicle (SSV) cyclooxygenase (95% pure, prostaglandin endoperoxide synthase, EC 1.14.99.1 specific activity 24 units/mg protein) obtained as a lyophilized powder from Biomol (Plymouth Meeting, Pa.) was reconstituted at a concentration of 59 mg/mL in Hanks' Balanced Salt Solution (HBSS). The enzyme was divided into 200 μL aliquots, snap frozen with liquid $N_2$, and stored at −70° C. until immediately prior to use. Measurements of CO activity were carried out in polypropylene tubes containing 495 μL of HBSS to which was added 5 μL of inhibitor or dimethylsulfoxide (DMSO; vehicle control) and 6 μL of SSV CO solution. The tubes were mixed on a vortex shaker, preincubated for 5 min at 37° C. prior to the initiation of the reaction. The s reaction was started by the addition of

[$^{14}$C]-arachidonic acid (1-$^{14}$C-AA, Amersham, Arlington Heights, Ill.) in 10 μL of methanol. Tubes were again vortexed and incubated in a water bath for 20 minutes after which the tubes were removed and the reaction stopped by acidification with the addition of 1 mL 2M formic acid. Lipophilic products were extracted with 3 mL chloroform and concentrated to dryness under $N_2$. Each pellet was reconstituted with 40 μL of chloroform and spotted on a Whatman Silicon thin-layer chromatography plate and developed in a chromatography tank containing A-9 solvent (11:5:2:1 V:V:VV, ethyl acetate:trimethyl-pentane:acetic acid:double distilled-$H_2O$). Radioactive cyclooxygenase products (prostaglandin $D_2$, prostaglandin $E_2$, etc.) were measured using a Bioscan System 200 Imaging Scanner. Inhibition of enzyme activity was calculated by comparing the areas under the curve produced in the presence or absence of test compound.

Procedure II was used to assess cyclooxygenase 1 activity (6226). Rat basophilic leukemia cells (RBL-1; 5×10$^7$ viable cells/mL) were disrupted by homogenization on ice (four 20 sec bursts) with a Brinkman polytron. Complete cell breakage was verified microscopically. The homogenate was then centrifuged at 9,220× g for 48 minutes at 4° C. The pellet was discarded and the supernatant was saved as the source of enzymes. The supernatant was pre-incubated for five minutes at 37° C. in the presence of 2 mM of CaCl2 and compound or vehicle (1% DMSO). The conversion of AA into products by CO and LO was initiated by adding 10 μL (50 μCi) of 1-$^{14}$C-AA to each tube and incubated at 37° C. for 20 minutes. The reaction was stopped by adjusting the pH of each sample to 3 to 3.5 with 2 M formic acid. Samples were extracted with three volumes of chloroform to isolate the products of 5-LO formed during the reaction. Fractions were dried under nitrogen, then resuspended in 40 μL of chloroform and spotted onto silica gel HL plates.

The plates were developed in A-9 solvent. The dried plates were analyzed using a Bioscan Imaging TLC scanner to determine the percentage of radiolabelled AA converted to 5-HETE (LO product) in each sample. The percentage of inhibition was calculated by:

[1-(5-HETE test)]/5-HETE control×100=% inhibition

The IC$_{50}$ was determined using a curve fit in Cricket Graph (Computer Associated), which provided the equation of the regressed line used in the calculation.

TABLE II

Biological Activities of Representative Compounds

| Example | X | Y | 6217 (COX-2) Wh Cell 1% @ 10?M | 6218 (COX-2) Wh Cell IC$_{50}$ (?M) | 6226 (COX-1) IC$_{50}$ (?M) |
|---|---|---|---|---|---|
| 1 | 4-Cl | 4-Cl |  | 0.34 | >10 |
| 2 | H | H | 54 | 10 | >10 |
| 3 | 4-Cl | H |  | 0.33 | >10 |
| 4 | H | 4-CH$_3$ |  | 0.33 | >10 |
| 5 | H | 4-Cl |  | 0.53 | >10 |
| 6 | H | 4-SO$_2$Me |  | >10 | >10 |
| 7 | 4-Cl | 4-Me |  | 0.01 | >10 |
| 8 | 4-Cl | 4-SO$_2$Me |  | >10 | >10 |

TABLE II-continued

Biological Activities of Representative Compounds

| Example | X | Y | 6217 (COX-2) Wh Cell 1% @ 10?M | 6218 (COX-2) Wh Cell IC$_{50}$ (?M) | 6226 (COX-1) IC$_{50}$ (?M) |
|---|---|---|---|---|---|
| 9 | 4-MeO | 4-Cl |  | 0.47 | >10 |
| 10 | 4-Cl | 4-OMe |  | 0.13 |  |
| 11 | 4-OMe | H |  | >10 | >10 |
| 12 | H | 4-OMe |  | 0.18 | >10 |

For use in the present invention, the compounds of Formula I may be used as the free base or as suitable pharmaceutical salts. Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The hydrazide compounds of the invention are capable of inhibiting the cycolooxygenase 2 (COX-2) enzyme pathway to achieve the desired pharmacological result. In preferred practice, the substituted cycloalkanopyrazole compounds of the pharmaceutical composition is capable of inhibiting the cyclooxygenase 2 enzyme pathway in the amount in which the compound is present in the composition, when the composition is administered as a unit dose in the appropriate mammal to be treated.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.01 mg/kg to about 500 mg/kg of animal body weight, preferably given in divided doses two to four times a day, or in sustained release form. For most large mammals the total daily dosage is from about 10 to about 2000 milligrams, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. Veterinary dosages correspond to human dosages with the amounts administered being in proportion to the weight of the animal as compared to adult humans.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

What is claimed is:

1. A method to alleviate inflammation in a mammal exhibiting an inflammatory condition, the method comprising administering to the mammal an effective amount of a pharmaceutical composition containing a unit dose of a compound of formula I:

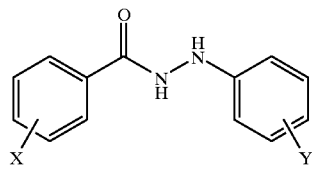

wherein:

X and Y are selected from hydrogen, halogen, alkyl, nitro, amino, hydroxy, methoxy and methylsulfonyl; or a pharmaceutically acceptable salt thereof, in association with a pharmaceutically acceptable carrier.

* * * * *